United States Patent [19]

Sakai et al.

[11] Patent Number: 4,540,794
[45] Date of Patent: Sep. 10, 1985

[54] METHOD FOR PREPARING 5-MERCAPTO-1,2,3-THIADIAZOLE SALTS

[75] Inventors: Kunikazu Sakai; Daiei Tunemoto; Takeo Kobori; Kiyoshi Kondo, all of Kanagawa, Japan

[73] Assignee: Lederle (Japan), Ltd., Tokyo, Japan

[21] Appl. No.: 532,922

[22] Filed: Sep. 16, 1983

[30] Foreign Application Priority Data

Sep. 17, 1982 [JP] Japan .............................. 57-160916

[51] Int. Cl.$^3$ ........................................... C07D 285/06
[52] U.S. Cl. .................................... 548/127; 564/94
[58] Field of Search ....................................... 548/127

[56] References Cited

U.S. PATENT DOCUMENTS 4,454,336  6/1984  Curran .................................. 560/13

OTHER PUBLICATIONS

March, Advanced Organic Chem., pp. 341-342, 373-376, (1977).

Primary Examiner—Robert Gerstl
Attorney, Agent, or Firm—Sughrue, Mion, Zinn, Macpeak, and Seas

[57] ABSTRACT

A method for preparing a 5-mercapto-1,2,3-thiadiazole salt represented by the general formula (I) is disclosed:

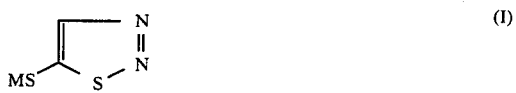

the method comprises the steps of:
providing a sulfonylhydrazone derivative represented by the general formula (II):

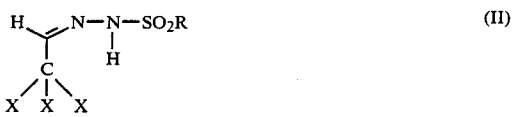

providing a sulfide represented by the general formula (III):

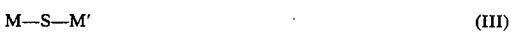

(wherein R is an aryl group, X is a chlorine or bromine atom, M is an alkali metal atom and M' is a hydrogen atom or an alkali metal atom);
combining the sulfonylhydrazone derivative represented by the general formula (II) and the sulfide represented by the general formula (III) and allowing a reaction to occur; and
obtaining the 5-mercapto-1,2,3-thiadiazole salt represented by the general formula (I).

11 Claims, No Drawings

METHOD FOR PREPARING 5-MERCAPTO-1,2,3-THIADIAZOLE SALTS

FIELD OF THE INVENTION

The present invention relates to a novel method for preparing a 5-mercapto-1,2,3-thiadiazole salt represented by the general formula (I):

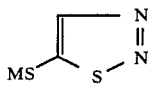
(I)

(wherein M is an alkali metal atom).

BACKGROUND OF THE INVENTION

The 5-mercapto-1,2,3-thiadiazole salt represented by the above general formula (I) obtainable by using the method of this invention are important compounds as modifier of cephalosporins [see G. S. Lewis and P. H. Nelson, J. Med. Chem., 1979, 22, 1214 and Japnese Patent Application (OPI) No. 59895/82 (the term "OPI" as used herein refers to a "published unexamined Japanese patent application") which corresponds to published unexamined British Patent Application No. 2083461 and Belgian Patent 88913].

Heretofore, the followings have been considered to be the best method for preparing 5-mercapto-1,2,3-thiadiazole salts: haloacetaldehyde is allowed to react with a semicarbazide or an alkoxycarbonylhydrazine to afford the corresponding hydrazone, then the hydrazone is converted to 5-chloro-1,2,3-thiadiazole by the action of thionyl chloride and the thiadiazole is treated with sodium sulfide to give a desired thiadiazole salt (see West German Patent Application (OLS) Nos. 2,636,994 and 2,856,404).

However, this method contains a drawback in that 5-chloro-1,2,3-thiadiazole formed as an intermediate is explosive (see S. Morisaki, Thermochim. Acta., 1981, 47, 85). Accordingly, considerable difficulties are involved with treatment and handling.

SUMMARY OF THE INVENTION

As a result of intensive studies on a safe and conventional method for the production of 5-mercapto-1,2,3-thiadiazole salts, the present inventors have achieved this invention.

This invention provides a method for preparing a 5-mercapto-1,2,3-thiadiazole salt represented by the general formula (I):

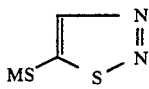
(I)

comprising the steps of:
providing a sulfonylhydrazone derivative represented by the general formula (II):

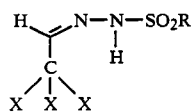
(II)

providing a sulfide represented by the general formula (III):

$$M-S-M' \quad (III)$$

(wherein R is an aryl group, X is a chlorine or bromine atom, M is an alkali metal atom and M' is a hydrogen atom or an alkali metal atom);
combining the sulfonylhydrazone derivative represented by the general formula (II) and the sulfide represented by the general formula (III) and allowing a reaction to occur; and
obtaining the 5-mercapto-1,2,3-thiadiazole salt represented by the general formula (I).

DETAILED DESCRIPTION OF THE INVENTION

The starting material of the present invention, i.e., a sulfonylhydrazone derivative represented by the above general formula (II) is easily obtained by the method described in the literature (K. Bott, Chem. Ber., 1975, 108, 402). For example, the sulfonylhydrazone derivatives derived from an acetaldehyde selected from tribromoacetaldehyde or trichloroacetaldehyde and the hydrazone selected from toluenesulfonylhydrazone, benzenesulfonylhydrazone, halobenzenesulfonylhydrazone, nitrobenzenesulfonylhydrazone, naphthylsulfonylhydrazone and the like can be used. The sulfonylhydrazone derivatives derived from trichloroacetaldehyde and the hydrazone selected from toluenesulfonylhydrazone or benzenesulfonylhydrazone are preferred.

As the sulfide represented by the general formula (III), sodium sulfide, potassium sulfide, sodium hydrosulfide, potassium hydrosulfide and the like can be used. Sodium sulfide is preferred. The sulfide is used in an amount of not less than 3 molar equivalents to the hydrazone derivative represented by the above general formula (II), preferably an amount of 3.5 to 5 molar equivalents from economical viewpoint, etc.

The reaction of the present invention is preferably carried out in solvent. The following solvents can be used independently or as mixture: water, alcoholic solvents such as methanol, ethanol, isopropanol, ethylene glycol, etc., and amine solvents such as pyridine, triethylamine, etc.

The reaction proceeds smoothly at atmospheric pressure at −10° C. to 60° C. and is preferably carried out at 0° C. to room temperature (about 25° C.) owing to the easy operation.

A 5-mercapto-1,2,3-thiadiazole salt represented by the above general formula (I) obtainable by this invention can easily be separated from a salt of sulfinic acid formed as by-product depending on the difference of solubility to alcoholic solvents. Furthermore, the above 5-mercapto-1,2,3-thiadiazole salt can be treated with an alkylating agent such as benzyl chloride or an acylating agent such as acetyl chloride to protect the mercapto group and thus can be isolated as a precursor of the desired 5-mercapto-1,2,3-thiadiazole.

The literature (K. Bott, Chem. Ber., 1975, 108, 402) discloses that a starting material of this invention, i.e., a sulfonylhydrazone derivative represented by the above general formula (II) can be converted, with the treatment of base, to a compound represented by the general formula:

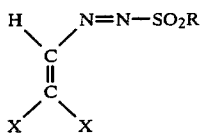

(wherein R is an aryl group, X is a chlorine or bromine atom). This compound is also allowed to react with a sulfide represented by the above general formula (III) and a similar reaction to one of this invention proceeds to afford a 5-mercapto-1,2,3-thiadiazole salt represented by the above general formula (I).

The present invention will be further explained in detail by Examples embodying the invention and Reference Examples below.

EXAMPLE 1

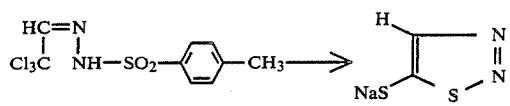

To 50% aqueous ethanol (40 ml) was dissolved 18.0 g (74.9 mmol, 3.75 mol eq) of sodium sulfide ($Na_2S.9H_2O$) and the solution was stirred under ice cooling. Powdered trichloroacetaldehyde p-toluenesulfonylhydrazone (6.31 g, 20.0 mmol) was added portionwise to the solution over the period of 5 min. After having been stirred for ca. 10 min, the reaction mixture was allowed to warm to room temperature and further stirred for 1 hr. The solvent was removed at 50° C. under reduced pressure and crystals were precipitated when the reaction mixture was concentrated to ca. one-third of its original volume. The mixture was allowed to stand under ice cooling and the crystals precipitated were collected by filtration. After being dried in a desiccator, the crystals were dissolved in ethanol (100 ml) and treated with active charcoal. The active charcoal was filtered off, the filtrate was concentrated to ca. 50 ml and allowed to stand. Sodium salt of p-toluenesulfinic acid was crystallized and filtered off. The filtrate was further concentrated and allowed to stand to precipitate the (above) sodium salt as crystals which was then filtered off. After confirmation of the absence of p-toluenesulfinic acid salt by measuring the NMR (spectrum) of one portion of the filtrate, the filtrate was again treated with active charcoal. Removal of the solvent afforded sodium salt of 5-mercapto-1,2,3-thiadiazole (1.68 g) as pale yellow crystals (yield 60%). This product was identical to an authentic sample when their IR spectra were compared. Sodium salt of p-toluenesulfinic acid (3.00 g) was isolated in total (yield 84%).

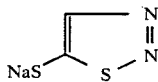

IR Spectrum (KBr disc, $cm^{-1}$): 3350, 1665, 1640, 1400, 1200, 1120, 1040, 870, 820.

NMR Spectrum ($D_2O$, TSP Deuterated, δ ppm) 8.2 (s).

EXAMPLE 2

Trichloroacetaldehyde p-toluenesulfonylhydrazone (3.1 g, 10 mmol) was added portionwise to a 50% aqueous ethanolic solution (50 ml) of 8.4 g of sodium sulfide ($Na_2S.9H_2O$). After having been stirred at room temperature for 2 hr, the reaction mixture was concentrated under reduced pressure and crystals precipitated were collected by filtration. The crystals were dried over potassium hydroxide under reduced pressure. Isopropanol (17 ml) was added to the crystals. The mixture was stirred at room temperature and undissolved substance was filtered off. The filtrate was treated with active charcoal, heated at 50° C. and then the filtrate was filtered. Crystals were precipitated by allowing the filtrate to stand for 16 hr. After removal of the crystals by filtration and evaporation of the solvent under reduced pressure, sodium salt of 5-mercapto-1,2,3-thiadiazole (0.59 g) was obtained as powdery crystals (yield 42%).

EXAMPLE 3

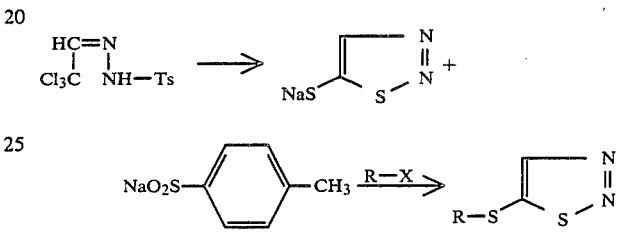

Powdered trichloroacetaldehyde p-toluenesulfonylhydrazone (6.31 g, 20.0 mmol) was added portionwise to a 50% aqueous ethanolic solution (40 ml) of 15.0 g (62.5 mmol) of sodium sulfide ($Na_2S.9H_2O$). After having been stirred at room temperature for 14 hr, the reaction mixture was concentrated to ca. one-third of its original volume under reduced pressure. Crystals precipitated after ice cooling were collected by filtration and dried to give 6.18 g of brown powdery crystals. It is confirmed based on NMR analysis of the aqueous solution of this product that this one is composed of sodium salt of 5-mercapto-1,2,3-thiadiazole and sodium salt of p-toluenesulfinic acid. The following alkylation was carried out using this mixture.

(a) R-X is benzyl bromide

Above mixture (1.00 g) was dissolved into 50% aqueous ethanol (6 ml) and benzyl bromide (806 mg, 4.71 mmol) was added to the solution at room temperature. After 1 hr of stirring, the reaction mixture was extracted with methylene chloride. The organic layer was washed with sat. aq. sodium chloride and dried over sodium sulfate. Evaporation of the solvent afforded 1.123 g of residue. This residue was purified by column chromatography ($SiO_2$, 30 g, $CH_2Cl_2$) to afford 449 mg of 5-benzylthio-1,2,3-thiadiazole. At the same time, 315 mg of benzyl p-tolyl sulfone was isolated.

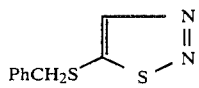

mp: 49° C.–51° C.

NMR ($CDCl_3$, TMS, δ ppm): 4.14 (2H, s), 7.30 (5H, s), 8.34 (1H, s).

MS (m/e): 208 ($M^+$, 2.3%), 180 (1.5%), 179 (5.3%), 147 (7.8%), 122 (15.1%), 91 (100%).

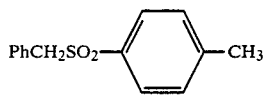

NMR (CDCl₃, TMS, δ ppm): 2.39 (3H, s), 4.25 (2H, s), 6.95–7.55 (9H, m).

(b) R-X is benzyl chloride

Above mixture (1.00 g) was dissolved into 50% aqueous ethanol (5 ml) and benzyl chloride (400 mg, 3.2 mmol) was added to the solution under ice cooling. After 2 hr stirring under ice cooling, the reaction mixture was extracted with ether. The ethereal layer was washed with sat. aq. sodium chloride and dried over sodium sulfate. Removal of the solvent under reduced pressure and drying under vacuum afforded 476 mg of 5-benzylthio-1,2,3-thiadiazole alone as crystals.

(c) R-X is ethyl β-bromopropionate

Above mixture (1.00 g) was dissolved into 50% aqueous ethanol (6 ml). Ethyl β-bromopropionate (570 mg) was added to the solution and the whole was stirred for 1 hr. The reaction mixture was extracted with ether. After the ethereal layer was treated in a similar manner as described in (b), excess of ethyl β-bromopropionate was removed under reduced pressure and 343 mg of 5-(2-ethoxycarbonylethyl)thio-1,2,3-thiadiazole alone was obtained as an oil.

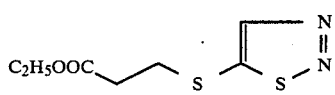

NMR (CDCl₃, TMS, δ ppm): 1.29 (3H, t), 2.71 (2H, t), 3.31 (2H, t), 4.17 (2H, q), 8.46 (1H, s).

(d) R-X is bromoethane

Above mixture (500 mg) was dissolved into 50% aqueous ethanol (3 ml). Bromoethane (0.5 ml) was added and the whole was stirred for 1 hr. The reaction mixture was treated in a similar manner as described in (b) to give 133 mg of 5-ethylthio-1,2,3-thiadiazole alone.

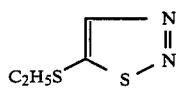

NMR (CDCl₃, TMS, δ ppm): 1.43 (3H, t), 3.08 (2H, q), 8.42 (1H, s).

EXAMPLE 4

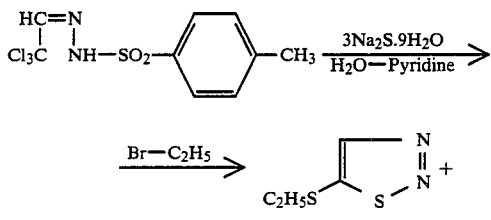

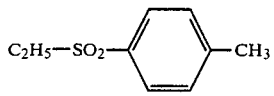

To a 30% aqueous pyridine solution (10 ml) of 721 mg (3.00 mmol) of sodium sulfide (Na₂S.9H₂O) was added powdered trichloroacetaldehyde p-toluenesulfonylhydrazone (316 mg, 1.00 mmol) and the whole was stirred for 10 hr. To this mixture was added bromoethane (1.0 ml) and the whole was stirred for 4 hr. Then, the reaction mixture was extracted with ethyl acetate. The organic layer was washed with sat. aq. sodium chloride and dried over sodium sulfate. Removal of the solvent under reduced pressure afforded 228 mg of oily substance which was confirmed, based on NMR analysis, to be a mixture of 5-ethylthio-1,2,3-thiadiazole and ethyl p-tolyl sulfide.

EXAMPLE 5

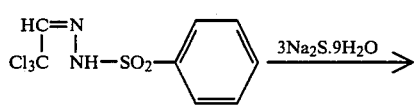

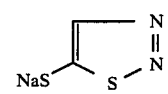

To a 50% aqueous ethanolic solution (100 ml) of 16.8 g (70 mmol) of sodium sulfide (Na₂S.9H₂O) was added portionwise trichloroacetaldehyde benzenesulfonylhydrazone (6.03 g, 20 mmol) under ice cooling. After having been stirred for 2 hr at room temperature, the reaction mixture was analyzed by NMR spectroscopy to confirm that the mixture contained 30% of 5-mercapto-1,2,3-thiadiazole anion.

EXAMPLE 6

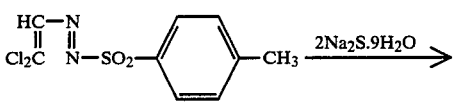

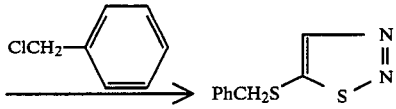

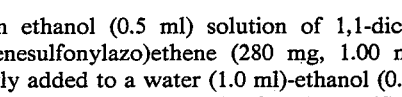

An ethanol (0.5 ml) solution of 1,1-dichloro-2-(p-toluenesulfonylazo)ethene (280 mg, 1.00 mmol) was slowly added to a water (1.0 ml)-ethanol (0.5 ml) solution of 600 mg (2.50 mmol) of sodium sulfide (Na₂S.9H₂O) under ice cooling. After 1 hr stirring at room temperature, the reaction mixture was cooled with ice. Benzyl chloride (0.5 ml) was added to the mixture and the whole was stirred for 1 hr. The reaction mixture was extracted with ether. The ethereal layer was washed with sat. aq. sodium hydrogen carbonate and sat. aq. sodium chloride, and then dried over sodium sulfate. After removal of the solvent by distillation, the residual oil was heated at 60° C. under vacuum to remove benzyl chloride and 94 mg of 5-benzylthio-1,2,3-thiadiazole was obtained as orange crystals (yield 45%).

While the invention has been described in detail and with reference to specific embodiments thereof, it will be apparent to one skilled in the art that various changes and modifications can be made therein without departing from the spirit and scope thereof.

What is claimed is:

1. A method for preparing a 5-mercapto-1,2,3-thiadiazole salt represented by the general formula (I):

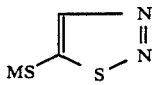
(I)

comprising the steps of:
providing a sulfonylhydrazone derivative represented by the general formula (II):

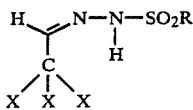
(II)

providing a sulfide represented by the general formula (III):

(III)

(wherein R is an aryl group, X is a chlorine or bromine atom, M is an alkali metal atom and M' is a hydrogen atom or an alkali metal atom);
combining the sulfonylhydrazone derivative represented by the general formula (II) and the sulfide represented by the general formula (III) and allowing a reaction to occur; and
obtaining the 5-mercapto-1,2,3-thiadiazole salt represented by the general formula (I) wherein the sulfide represented by the general formula (III) is present in an amount of not less than 3 molar equivalents based on the amount of the sulfonylhydrazone derivative represented by the general formula (II).

2. A method for preparing a 5-mercapto-1,2,3-thiadiazole salt as claimed in claim 1, wherein the sulfonylhydrazone derivative represented by the general formula (II) is a compound derived from an acetaldehyde selected from tribromoacetaldehyde or trichloroacetaldehyde and a hydrazone selected from toluenesulfonylhydrazone, benzenesulfonylhydrazone, halobenzenesulfonylhydrazone, nitrobenzenesulfonylhydrazone or naphthylsulfonylhydrazone.

3. A method for preparing a 5-mercapto-1,2,3-thiadiazole salt as claimed in claim 1, wherein the sulfide represented by the general formula (III) is a compound selected from the group consisting of sodium sulfide, potassium sulfide, sodium hydrosulfide and potassium hydrosulfide.

4. A method for preparing a 5-mercapto-1,2,3-thiadiazole salt as claimed in claim 3, wherein the sulfide represented by the general formula (III) is present in an amount in the range of 3.5 to 5 molar equivalents based on the amount of the sulfonylhydrazone derivative represented by the general formula (II).

5. A method for preparing a 5-mercapto-1,2,3-thiadiazole salt as claimed in claim 1, wherein the reaction is carried out in the presence of a solvent.

6. A method for preparing 5-mercapto-1,2,3-thiadiazole salt as claimed in claim 5, wherein the solvent is selected from the group consisting of water, alcoholic solvents and amine solvents.

7. A method for preparing a 5-mercapto-1,2,3-thiadiazole salt as claimed in claim 6, wherein the solvent is selected from the group consisting of water, methanol, ethanol, isopropanol, ethylene glycol, pyridine and triethylamine.

8. A method for preparing a 5-mercapto-1,2,3-thiadiazole salt as claimed in claim 1, wherein the reaction is carried out at temperature in the range of −10° C. to 60° C.

9. A method for preparing a 5-mercapto-1,2,3-thiadiazole salt as claimed in claim 8, wherein the reaction is carried out at temperature in the range of 0° C. to about 25° C.

10. A method for preparing a 5-mercapto-1,2,3-thiadiazole salt as claimed in claim 1, wherein the 5-mercapto-1,2,3-thiadiazole salt represented by the general formula (I) is separated from a salt of sulfinic acid depending on the difference of solubility to alcoholic solvents.

11. A method for preparing a 5-mercapto-1,2,3-thiadiazole salt represented by the general formula (I):

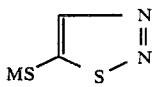
(I)

comprising the steps of:
providing a sulfonylhydrazone derivative represented by the general formula (IV):

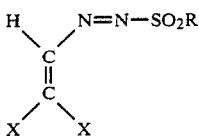
(IV)

providing a sulfide represented by the general formula (III):

(III)

wherein R is an aryl group, X is a chlorine or bromine atom, M is an alkali metal atom and M' is a hydrogen atom or an alkali metal atom);
combining the sulfonylhydrazone derivative represented by the general formula (IV) and the sulfide represented by the general formula (III) and allowing a reaction to occur; and
obtaining the 5-mercapto-1,2,3-thiadiazole salt represented by the general formula (I);
wherein the sulfide represented by the general formula (III) is present in an amount of not less than 3 molar equivalents based on the amount of the sulfonylhydrazone derivative represented by the general formula (IV).

* * * * *